US005872108A

United States Patent [19]
Sandage, Jr. et al.

[11] Patent Number: 5,872,108
[45] Date of Patent: *Feb. 16, 1999

[54] REDUCTION OF INFARCT VOLUME USING CITICOLINE

[75] Inventors: Bobby W. Sandage, Jr.; Marc Fisher; Kenneth W. Locke, all of Lexington, Mass.

[73] Assignee: Interneuron Pharmaceuticals, Inc., Lexington, Mass.

[*] Notice: The term of this patent shall not extend beyond the expiration date of Pat. No. 5,801,160.

[21] Appl. No.: 603,102

[22] Filed: Feb. 20, 1996

Related U.S. Application Data

[63] Continuation-in-part of Ser. No. 399,262, Mar. 6, 1995, abandoned.

[51] Int. Cl.$^6$ .................................................. A61K 31/70
[52] U.S. Cl. .......................................................... 514/49
[58] Field of Search ................................................ 514/49

[56] References Cited

U.S. PATENT DOCUMENTS 4,386,078   5/1983   Horrocks et al. ........................ 424/180

OTHER PUBLICATIONS

HCAPLUS abstract, AN 1988:143195, Kakihana, M. et al. (1988).
Longa, Zea et al., *Stroke* (1989) 20:84–91.
The Ancrod Study Investigators, *Stroke* (1994) 25:1755–1759.
Budavari et al., *The Merck Index (11th Ed.)* pp. 361–362, 1995.
Rossi, M. et al., *Medline Abstract* 93230870 (Feb. 1993).
Canino, V. et al., *Medline Abstract* 80188636 (1980).
Giratto, T. et al., *Embasse Abstract* 71026199 (1980).
Kaste, M. et al. *Stroke* (1994) 25:1348–1353.
Olney, J.W. et al. *Science* (1991) 254:1515–1518.
Kinouchi, H. et al. *Proc. Natl. Acad. Sci. USA* (1991) 88:11158–11162.
Diener, H.C. et al. *Stroke* (1995) 26:30.
Bell, R.D. et al. *Stroke* (1991) 22:80–83.
del Zoppo, G.J. et al. *Seminars in Neurology* (1991) 11(4): 368–384.
The Ancrod Stroke Study Investigators, *Stroke* (1994) 25:1755–1759.
Hacke, W. et al. *Stroke* (1995) 26:167.
Ulus, I.H. et al. *Brain Research* (1989) 484:217–227.
Altman R. et al. *British Medical Journal* (1994) 308:81–106.
The Canadian Cooperative Study Group, *New England Journal of Medicine* (1978) 299:53–59.
The ESPS Group, "The European Stroke Prevention Study." (1990) *Stroke* 21:1122–1130.
Minematsu, K. et al. *Cerebrovasc. Dis.* (1993) 3:99–104.
Schabitz, W. et al. *Journal of the Neurological Sciences* (1996) 138:21–25.

D'Orlando, K.J. et al. *Neurological Research* (1995) 17:281–284.
Abstract: "Effects of Citicoline on infarct volume, mortality and behavioral outcome after temporary local ischemia" by: Johannes Weber et al., dated: Jan. 9, 1995, European Stroke Conference, Bordeaux, France Jun. 1–3, 1995.
Kogure, K., et al., *Annals of Neurology*, vol. 8, No. 3, Sep. 1980, pp. 278–290.
Grosset, D.G., et al., *Journal of Cardiovascular Pharmacology*, vol. 25, No. 5, 1995, pp. 705–709.
Lo, Eng H., *Neuroscience Letters*, 131, (1991), pp. 17–20.
McCulloch, J., et al., *Acta Neurochir*, (1993)[Suppl] 57:73–79.
Tuor, U.I., et al., *Stroke*, vol. 24, No. 3, Mar. 1993, pp. 452–457.
Grotta, James, *Stroke*, Vo. 18, No. 1, Jan.–Feb. 1987, pp. 264–267.
Ochiai, Chikayuki, et al., *Stroke*, Vo. 13, No. 6, Nov.–Dec. 1982, pp. 788–796.
Barinaga, *Science*, vol. 272, May 3, 1996, pp. 664–666.
Demeurisse, G., et al., *Stroke*, vol. 14, No. 1, Jan.–Feb. 1983, pp. 77–81.
Windholtz et al. (eds.), *The Merck Index*, 19$^{th}$ Ed., Merck & Co., Inc. Rahway, NJ, 1983, entry 2290 at p. 329.
Makishima et al., "Treatment of Sensory–Neural Deafness and Tinnitus with a Nucleic Acid Derivative," *Arzeneimittel Forsch. Dtsh.*, 21,(9),1343–1349 (1971).
Nilsson, "CDP–Choline–A Short Review," *Clin. Pharmacol. Drug Epidemiol.* 2, 273–277 (1979).
Phuong et al., "Nouvell Méthode de Préparation de al Cytidine Diphosphate Choline (CDP Choline)", *Bull. Soc. Chim. Fr. Pt. II.*, 1979(9–10), 518–519.
Gannaro et al. (eds.), *Remmington's Pharmaceutical Sciences*, 18$^{th}$ ed., Mack Publishing Co., Easton, PA, 1990, see pp. 867, 1014 and 1026 as marked.
Sanchez et al., "CDP–Choline:Physico–Chemical Characteristics," *Arzneimittel Forschung—Drug Research*, 33(II), 1011–1012(1983).
Algate et al., "Study of the Effects of Oral Administration of CDP–Choline on EEG Changes and Lethality Induced by Epidural Compressions in the Anaethestized Cat." *Arzneimittel Forschung—Drug Research*, 33(II), 1013–1016(1983).

(List continued on next page.)

*Primary Examiner*—Marianne M. Cintins
*Assistant Examiner*—M. Moezie
*Attorney, Agent, or Firm*—Gilberto M. Villacorta, Pepper Hamilton LLP

[57] ABSTRACT

The invention is directed to a method of reducing the extent of infarction, particularly cerebral infarction subsequent to cerebral ischemia, by the administration of citicoline shortly after an ischemic episode and continuing daily treatment for up to about 30 days, preferably for at least about 6 weeks. The method is useful in the treatment of stroke and severe head trauma patients and maximizes the chances for a full or substantially full recovery of the patient.

17 Claims, 1 Drawing Sheet

OTHER PUBLICATIONS

Agut et al.(I), "Dissimilar Effects in Acute Toxicity Studies of CDP–Choline and Choline," *Arzneimittel Forschung—Drug Research,* 33(II), 1016–1018(1983).

Braso et al., "Action of CDP–Choline by Intraduodenal Route on Rat Cardiorespitory System," *Arzneimittel Forschung—Drug Research,* 33(II), 1043–1045(1983).

Agut et al. (III), "Radioactivity Incorporation into Different Cerebral Phospholipids after Oral Administration of $^{14}C$ Methyl CDP–Choline," *Arzneimittel Forschung—Drug Research,* 33(II), 1048–1050(1983).

Agut et al.(II, "Bioavailability of Methyl $-^{14}C$ CDP–Choline and Choline by Oral Route." *Arzneimittel Forschung—Drug Research,* 33(II), 1045–1047(1983).

Aguilar et al., "Cerebral Subcellular Distribution of CDP–Choline and/or its Metabolites after Oral Administration of Methyl–$^{14}C$ CDP–Choline," *Arzneimittel Forschung—Drug Research,* 33(II), 1051–1053(1983).

Romero et al.(I), "Low–Resolution Autoradiography in Rat Brain after Administering Labeled CDP–Choline Administration," *Arzneimittel Forschung—Drug Research,* 33(II), 1054–1056(1983).

Romero et al.(II), "High–Resolution Autoradiography in Mouse Brain 24 h after Radiolabelled CDP–Choline Administration," *Arzneimittel Forschung—Drug Research,* 33(II), 1056–1058(1983).

Romero et al. (III), "High–Resolution Autoradiography in Mouse Brain and Cerebellum 10 days after Radiolabelled CDP–Choline Administration," *Arzneimittel Forschung—Drug Research,* 33(II), 1058–1060(1983).

Dinsdale et al. (I), "CDP–Choline Repeated Oral Dose Tolerance Studies in Adult Healthy Volunteers," *Arzneimittel Forschung—Drug Research,* 33(II), 1061–1065 (1983).

Arrannz et al. "Treatment of Chronic Dyskinesia with CDP–Choline," *Arzneimittel Forschung—Drug Research,* 33(II), 1071–1073(1983).

Tornos et al. (I), "Effect of Oral CDP–Choline on Experimental Withdrawal Syndrome," *Arzneimittel Forschung—Drug Research,* 33(II), 1018–1021(1983).

Tornos et al. (II), "Pharmacological Study of CDP–Choline," *Arzneimittel Forschung—Drug Research,* 33(II), 1022–1024(1983).

Grau et al.(I), "Study on the Protection of CDP–Choline against Nicotine Intoxification," *Arzneimittel Forschung—Drug Research,* 33(II), 1025–1026(1983).

Tornos et al. (III), "Pharmacological Study of Oral CDP–Choline," *Arzneimittel Forschung—Drug Research,* 33(II), 1026–1029(1983).

Agut et al. (IV), "Effect of Oral CDP–Choline on Acrylamide–induced Lesion." *Arzneimittel Forschung—Drug Research,* 33(II), 1029–1033(1983).

Grau et al. (II), "CDP–Choline: Acute Toxicity Study," *Arzneimittel Forschung—Drug Research,* 33(II), 1033–1034(1983).

Romero et al. (IV), "Study of Subacute Toxicity of CDP–Choline after 30 days of Oral Administration to Rates," *Arzneimittel Forschung—Drug Research,* 33(II), 1035–1038 (1983).

Romero et al. (V), "CDP–Choline: 6–Month Study on Toxicity in Dogs," *Arzneimittle Forschung—Drug Research,* 33(II), 1038–1042(1983).

Dinsdale et al. (II), "Pharmacokinetics of $^{14}C$ CDP–Choline," *Arzneimittel Forschung—Drug Research,* 33(II), 1066–1070(1983).

Fernandez, "Efficacy and Safety of Oral CDP–Choline," *Arzneimittel Forschung—Drug Research,* 33(II), 1073–1080(1983).

Table of Contents, Key Word Index and Preface[a] (J.A. Ortiz) Introducing the Series of Papers on Cytidine Diphosphate Choline, *Arzneimittel Forschung—Drug Research,* 33(II), 1009–1010[a] (1983) and preceding pages.

Cohen et al., "Decreased Brain Choline Uptake in Older Adults–An In Vivo Proton Magnetic Resonance Spectroscopy Study," *J. Am. Medical Association,* 274(11),902–907(1995).

Fukunaga et al. (I). "Hypotensive Effects of Adenosine and Adenosine Triphosphate Compared with Sodium Nitroprusside," *Anesthesia and Analgesia,* 61(3), 273–278 (1982).

Trovarelli, G. et al., "Effect of Cytidine on the Modification of Phospholipid Metabolism Induced by Ischemia", *Neurochemical Research,* vol. 12, No. 3, 1987, pp. 227–235.

Trovarelli, G. et al., "The Influence of Cytidine on the Endogenous Pool of CDP–Choline, CDP–Ethanolamine, and CMP of the Rat Brain", *Neurochemical Research,* vol. 9, No. 1, 1984, pp. 73–79.

Trovarelli, G. et al., "The Transport of Cytidine into Rat Brain In Vivo, and its Conversion into Cytidine Metabolites", *Neurochemical Research,* vol. 7, No. 10, 1982, pp. 1199–1207.

De Medio, G.E. et al., "The Effect of Cytidine–Diphosphate Choline (CDP–Choline) on Brain Lipid Changes During Aging", *Journal of Neuroscience Research,* 11:49–58 (1984).

Petkov, V.D. et al., "Effects of Cytidine Diphosphate Choline on Rats with Memory Deficits", *Institute of Phisiology, Bulgarian Academy of Science, Sofia, Bulgaria,* pp. 822–828, (1993).

Kottler, P.D. et al., "RNA Metabolism in the Rat Brain During Learning Following Intravenous and Intraventricular Injections of 3H–Cytidine", *Physiology and Behavior,* vol. 8, pp. 219–297 (1992).

Wurtman, R.J. et al., "The 'Autocannibalism' of Choline–Containing Membrane Phospholipids in the Pathogenesis of Alzheimer's Disease", *Dept. of Applied Biological Sciences, Cambridge, MA, USA and Pharmacology Department, Universite, Suisse* Neurochem. Intl., pp. 369–372 (1985).

Buyukuysal, R.L. et al., "4–Aminopyridine Increases Acetylcholine Release Without Diminishing Membrane Phosphatidylcholine", *Journal of Neurochemistry,* vol. 54, No. 4, 1990, pp. 1302–1309.

Savei, V. et al., "Effect of Cytidine on Membrane Phospholipid Synthesis in Rat Striatal Slices", *Journal of Neurochemistry,* vol. 64, No. 1, 1995, pp. 378–384.

REDUCTION OF INFARCT VOLUME USING CITICOLINE

The present application is a continuation-in-part of U.S. application Ser. No. 08/399,262, filed Mar. 6, 1995, now abandoned the entire disclosure of which is incorporated by reference herein.

FIELD OF THE INVENTION

The present invention relates to a method of reducing the extent of infarction, particularly cerebral infarction, subsequent to an ischemic event. Reduction of the infarct volume, possibly coupled with facilitated repair of any damaged tissue, may, in turn, maximize the potential for recovery following loss of critical blood flow, such as the condition that may follow a stroke. More particularly, the invention relates to the use of citicoline (cytidine-diphosphate CDP-choline) in a novel treatment regimen to reduce cerebral infarct volume and improve the chances for complete or substantial recovery.

BACKGROUND OF THE INVENTION

The brain, more than any other organ in the body, depends, for its survival and proper functioning, on a relatively constant supply of oxygenated blood. While comprising only 2% of the body's weight, the brain receives 15% of the heart's output of blood and consumes 20% of the oxygen used by the body. In addition, a constant supply of blood is required to provide the brain with glucose, the major energy substrate used by the brain to produce high energy phosphates such as ATP.

Ischemia may be defined as the loss of blood flow to a tissue. Cerebral ischemia is the interruption or reduction of blood flow in the arteries feeding the brain, usually as a result of a blood clot (thrombus) or other matter (embolus) occluding the artery. Loss of blood flow to a particular vascular region is known as focal ischemia; loss of blood flow to the entire brain, global ischemia.

Once deprived of blood—and, hence, oxygen and glucose—brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation.

Knowledge of these underlying events has led investigators studying certain types of ischemic injury to utilize agents such as calcium channel blockers, glutamate and glycine antagonists, CDP-amines, free radical scavengers/antioxidants, perfluorocarbons and thrombolytic agents to improve cerebral blood flow and/or neurological outcome, all with mixed results. Indeed, some vasodilators may improve blood flow and, thus, may find use as anti-ischemic agents. None, however, has been shown to reduce infract volume, particularly in patients that have suffered an ischemic stroke. Conversely, although certain calcium-channel blockers have been reported to decrease infarct size, these drugs also have been reported to produce inconsistent results and undesirable side effects, such as reduction in pulse or perfusion pressure. See, e.g., Kaste, M. et al. *Stroke* (1994) 25:1348–1353.

More particularly, glutamate antagonists have been observed to reduce infarct size under certain experimental conditions. See, e.g., Olney, J. W. et al. *Science* (1991) 254:1515–1518. However, most, if not all, of these compounds cause brain vacuolization and most produce phencyclidine-like subjective effects in animals and humans. Ingestion of phencyclidine has been associated with euphoria, anxiety, mood lability and prolonged psychosis.

Free radical scavengers/antioxidants are a heterogenous group of compounds. In general, the effects of these compounds on infarct volume have been inconsistent. For example, superoxide dismutase inhibitors have been found to reduce infarct volume only when injected intracerebroventricularly. See, Kinouchi, H. et al. *Proc. Natl. Acad. Sci. USA* (1991) 88:11158–11162. Other compounds, such as lubeluzole, have been shown to have clinical benefit but with a very narrow margin of safety. See, Diener, H. C. et al. *Stroke* (1995) 26:30.

Although perfluorocarbons have shown some benefit in the outcome from ischemic stroke, these compounds have an extremely long half-life and must be infused into the brain and spinal fluid. In addition, these compounds have been observed to cause gonadal hypertrophy. See, Bell, R. D. et al. *Stroke* (1991) 22:80–83].

Thrombolytic agents, such as t-PA (tissue plasminogen activator), streptokinase, and urokinase, have shown some promise in the treatment of ischemia. However, these agents have the propensity to increase intracranial bleeding, which, ultimately, can lead to increased mortality. See, e.g., del Zoppo, G. J. et al. *Seminars in Neurology* (1991) 11(4):368–384; *The Ancrod Stroke Study Investigators, Stroke* (1994) 25:1755–1759; Hacke, W. et al. *Stroke* (1995) 26:167. Moreover, the efficacy of these agents may be limited to treatment within the first three hours of stroke.

Citicoline monosodium is an exogenous form of cytidine-5'-diphosphocholine (CDP-choline). Endogenous CDP-Choline is a key intermediate in the biosynthesis of membrane phosphatidyl choline, which is of primary importance for the dynamic regulation of cellular integrity. The role of phospholipids in the maintenance of neuronal function is critically important in conditions where ischemia can induce the breakdown of these membranes.

Citicoline has been extensively studied in clinical trials. Results of these trials indicated an improvement in a variety of clinical symptoms, including headache, vertigo, motor coordination and insomnia. These trials also showed improvements in motor function and reduction in stroke sequelae. However, such trials were limited to the use of citicoline during the rehabilitation stage of patients who may have suffered a stroke, and, thus, such treatments occurred well after the putative ischemic event. Nevertheless, such trials showed that stroke and head trauma patients tolerated citicoline well at dose ranges of 250 mg/day to 1000 mg/day for several weeks.

The inventors believe that the full potential therapeutic effects of citicoline, which may be related to membrane stabilization through enhanced phospholipid synthesis in ischemic brain, have not been realized in prior studies because such studies involved the administration of citicoline well after the onset of ischemia, typically only during the treatment efforts to foster recovery of the patient. Furthermore, such prior treatments may not have proceeded for sufficiently long enough periods.

Stroke is a severe, potentially catastrophic disease affecting approximately 500,000 people per year in the U.S. Clinicians have had to rely on supportive measures and non-specific agents, such as steroids and mannitol, to reduce brain swelling. As 25 to 50% of stroke victims become disabled, there exists a need for improved methods of treating these patients.

Although intravenous thrombolytic therapy has shown some promise if administered within three hours of a stroke, it is believed that an oral drug treatment that would be initiated within a 24-hour post-stroke window and which would positively affect neurological outcome three months after a stroke could become an important new weapon in the fight against this disease.

SUMMARY OF THE INVENTION

The invention relates to a method for reducing infarct volume, particularly cerebral infarct volume, subsequent to an ischemic event, e.g., cerebral ischemia, caused by any of a number of disorders, such as ischemic stroke, comprising administering an effective amount of citicoline or a pharmaceutically-acceptable salt thereof. Such disorders include, but are not limited to, thromboembolic or hemorrhagic stroke, cerebral vasospasm, hypoglycemia, cardiac arrest, and status epilepticus, and also may include schizophrenia, epilepsy, neurodegenerative disorders, Alzheimer's disease, and Huntington's disease.

The present invention also relates to the use of citicoline for the preparation of a pharmaceutical medicament for the reduction of infarct volume, particularly the size of a cerebral infarct, comprising admixing an effective amount of citicoline with a pharmaceutically acceptable carrier.

In the method of reducing infarct volume or size, administration of an effective amount of citicoline must take place within a short time following the ischemic episode, preferably within a 24-hour window. Subsequent administrations of citicoline should then follow over a specified period, typically over at least about a one week (ca. 5–10 days, but preferably at least about 7 days), most preferably over at least about a few weeks to several weeks (e.g., 3–8 weeks, preferably at least about 6 weeks). The dosage regimen can vary within certain limits. Typically, about 100–2000 mg of citicoline can be administered one or more times per day, preferably once a day for the duration of the treatment period. Preferred single daily dosage includes about 500–1000 mg of citicoline, most preferably, about 500 mg. Again, however, this single dose may be administered more than once a day, e.g., twice a day, if desired.

Citicoline may be expected to have a number of advantages over other agents being developed for the reduction of infarct volume subsequent to an ischemic event. Being an endogenous compound, citicoline is inherently safe. Citicoline has a very low toxicity and an extremely broad therapeutic index.

The potential multimodal action of citicoline also may prove advantageous. Although the relative contribution of each potential mode of action to the reduction of infarct size is unknown, citicoline and its hydrolysis products—cytidine and choline—are believed to play important roles in the generation of phospholipids involved in membrane formation and repair. These compounds also are believed to contribute to critical metabolic functions, such as the formation of nucleic acids and proteins, and the synthesis of the neurotransmitter acetylcholine. See, Ulus, I. H. et al. *Brain Research* (1989) 484:217–227. Thus, under ischemic conditions, citicoline may function to (1) stabilize membranes by providing substrate for membrane maintenance; (2) repair damaged membranes by supplying important substrates for membrane formation; and (3) restore neuronal function by supplying substrate for the formation of acetylcholine. Moreover, unlike other, proposed therapeutic agents, citicoline has the potential not only to reduce initial infarct size, but also to contribute to the repair of the damaged area.

It is, therefore, one object of the invention to provide methods for improving the recovery of victims of stroke and head trauma. Hence, it is another object of the invention to administer citicoline to patients very soon after the onset of ischemia, preferably within 24 hours following the ischemic event. Most preferably, the first dose of citicoline is administered within about twelve hours to about fifteen hours of the ischemic event.

Yet another object of the invention is to provide methods for decreasing infarct volume in patients who have suffered injury, e.g., through an ischemic stroke or head trauma or any conditions that may lead to loss of blood flow in the affected organ or tissue.

These and other objects if the invention will be apparent to those of ordinary skill in view of the discussion above and the additional detailed description provided below relating to preferred embodiments of the invention.

DETAILED DESCRIPTION

Figure 1:
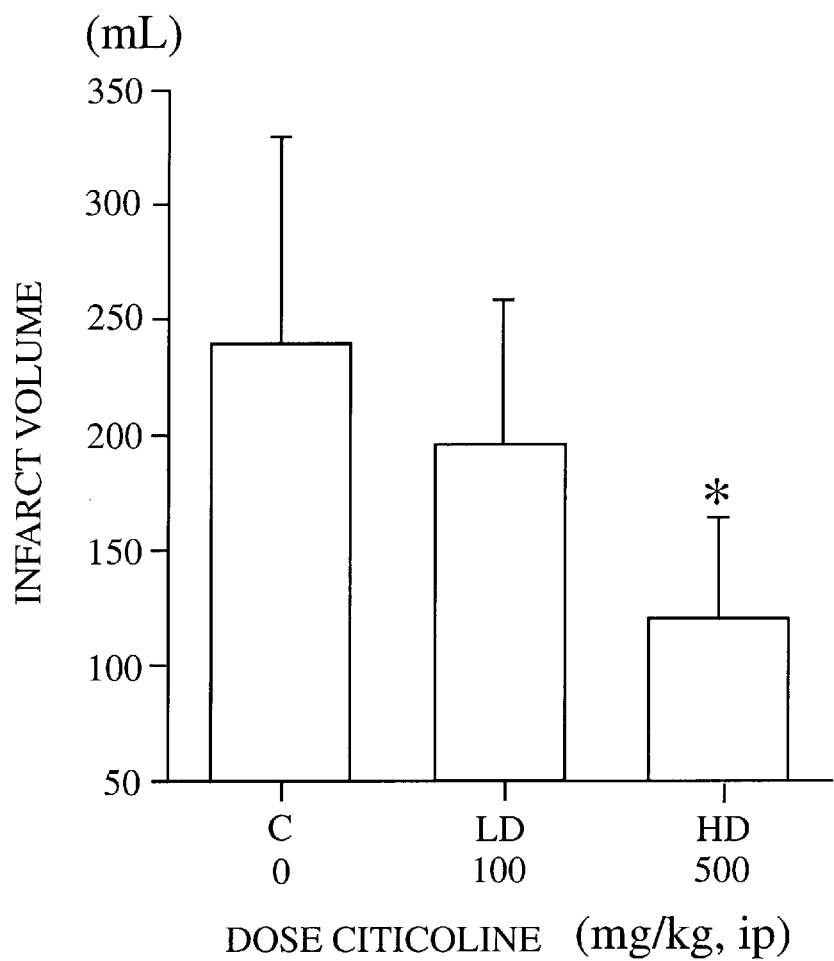
FIG. 1 depicts bar graphs of infarct volume in animal groups receiving vehicle control, 100 mg/kg citicoline, and 500 mg/kg citicoline. Values are mean±standard deviation (SD).

The present invention comprises a method for reducing infarct volume comprising the steps of administering citicoline, or a pharmaceutically acceptable salt thereof, in from one to four doses daily, at about 100 mg to 2000 mg per dose, beginning very soon after an ischemic event and continuing for at least up to about a week (e.g., seven days) to several weeks, preferably 4–8 weeks, more preferably 5–8 weeks, most preferably for at least about 6 weeks.

Without being limited by theory, it is believed that citicoline has at least a dual mechanism of action: limiting the brain damage caused by injuries such as stroke or severe head trauma and aiding in the repair of damaged neuronal tissues.

Administration of citicoline is believed to limit the extent of the infarct, or tissue damage, by preventing the accumulation of toxic free fatty acids. In addition, following its administration, it is believed that citicoline is broken down into two components, cytidine and choline, which are substrates required in the formation of nerve cell membranes. It is further postulated that to normalize brain function, nerve cells damaged by stroke must manufacture new membrane elements. As described below, in preclinical animal models of stroke, administration of citicoline is shown to significantly reduce infarct size. This result is confirmed in humans by the clinical investigation described further below in which a select group of patients undergoing early intervention by citicoline treatment is examined by magnetic resonance imaging techniques.

The present invention is directed to a new and important use of citicoline—the reduction of infarct size subsequent to cerebral ischemia. Although stabilization of membranes is believed to be of benefit in ischemic conditions, it has not been definitively demonstrated that membrane stabilization will lead to reduced infarct volume. The present inventors have unexpectedly found that administration of citicoline for just seven (7) days, significantly reduces infarct volume, presumably by altering phosphatidylcholine synthesis and membrane formation.

The cerebroprotective action of citicoline was demonstrated, in one case, in a model of temporary forebrain ischemia in the rat in which the middle cerebral artery (MCA) is occluded by suture. Treatment with 500 mg/kg of citicoline significantly reduced the mean volume of infarction compared with controls.

Citicoline is generally preferred to be administered orally as a pharmaceutically acceptable salt. The preferred salt is the monosodium salt of citicoline, as this form is readily available in pharmaceutically acceptable purity.

As mentioned above, treatment under the invention is preferably begun within at least about 24 hours from onset, preferably within about 12–15 hours of onset, most preferably begun as soon as possible after the initial ischemic episode. In a specific embodiment of the invention, treatment is continued for at least up to about 7 days, preferably at least up to about 14 days, most preferably at least up to about 30 days from the start of treatment.

Hence, according to one embodiment of the invention, a method is disclosed of reducing infarct volume in a patient who has experienced an ischemic event comprising administering a first dose of an effective amount of citicoline or a pharmaceutically acceptable salt thereof shortly after but no later than about 24 hours after the occurrence of the ischemic event, followed by the administration of subsequent doses of effective amounts of citicoline or a pharmaceutically acceptable salt thereof over a period of at least about a week. Preferably, the first dose is administered within about 12 to about 15 hours after the occurrence of the ischemic event and that the first dose is followed by subsequent doses of citicoline or a pharmaceutically acceptable salt thereof over a period of at least about 7 days, preferably 14 days, most preferably 30 days.

The preferred dose of about 500 to about 1000 mg of citicoline or its pharmaceutically acceptable salt may be administered one or more times daily, preferably once or twice a day.

The method of the present invention finds its most advantageous use in human patients who have experienced an ischemic event that has occurred in the brain, typically from a cerebral ischemia, head trauma, or the like. It cannot be stressed enough, however, that the administration of the first dose of an effective amount of citicoline or its pharmaceutically acceptable salt should transpire as soon as possible after the ischemic event but no more than about 24 hours after such occurrence.

A variety of dosage ranges are suitable. The citicoline dosage under the invention may be from about 100 mg to about 1000 mg from one to about 4 times per day. For example, when a single daily dose is desired, citicoline is administered in from about 100 to about 4000 mg per day, preferably from about 500 to about 2000 mg per day. In one embodiment of the invention, the dose is 1000 mg per day.

For medical use, the amount required of citicoline, or a pharmacologically-acceptable salt thereof ("the active ingredient") to achieve a therapeutic effect will vary with the route of administration and the particular disorder or disease to be treated. A suitable systemic dose of the active ingredient, for a mammal suffering from, or likely to suffer from, any of the conditions described herein, is in the range of 100 mg to 4000 mg per day, with a preferred dose of 1000 mg per day, administered 500 mg twice daily. A dose of 1000 mg citicoline per day will produce a plasma choline concentration of 1.5 ng/ml, the same as that produced by the administration of 500 mg/kg/day citicoline to the rat, as further described in the Examples. It is has been shown, however, that 500 mg per day conveys most of the benefits of citicoline treatment while minimizing any side effects, including dizziness, which may be experienced by some patients.

In the trial, two hundred fifty-nine patients with ischemic stroke were enrolled within 24 hours following the onset of symptoms. Patients were randomly assigned to receive placebo or one of three oral doses of citicoline (500 milligrams, 1000 milligrams or 2000 milligrams daily) for six weeks and were monitored for an additional six weeks. The primary efficacy outcome scale was improved neurologic function at 12 weeks after stroke, as assessed by the Barthel Index.

Patients who received 500 milligrams or 2000 milligrams of citicoline daily exhibited significantly greater ($p<0.05$) improvement on the Barthel Index at week 12 than placebo-treated patients. Efficacy outcome measures for the 1000 milligram daily group did not reach statistical significance, although demographic imbalances and confounding variables among patients in this group may ultimately explain this finding.

In addition, global neurologic status, assessed by another well-known measurement, the Rankin Scale, was significantly improved ($p<0.04$) with citicoline treatment compared to placebo.

The Barthel Index utilizes a 100-point rating scale. Scores of 95 or greater are indicative of complete or near-complete recovery from stroke. Overall, 33% of placebo-treated patients achieved a score of greater than 95 at 12 weeks after stroke, compared to 53% of patients who received 500 milligrams daily of citicoline ($p<0.04$).

Another outcome scale, the NIH Stroke Scale, showed that 34% of citicoline-treated patients versus 16% of placebo-treated patients achieved complete or near-complete normalization of function, as indicated by scores less than or equal to 1, at 12 weeks following stroke ($p<0.04$).

There was no significant difference in the incidence of death among the four treatment groups. Preliminary analysis of adverse events and laboratory findings revealed that all doses of citicoline were well tolerated. The only statistically significant differences among citicoline-treated patients versus placebo-treated patients were an increase in dizziness and accidental injuries, e.g., falling down. However, the 500 milligram dose citicoline group did not significantly differ from the placebo group in these parameters.

Given the degree of effectiveness of the 500 milligram daily dose and the absence of significant differences in adverse events between this dosage level and placebo, 500 milligrams daily appears to be the optimal dose derived from this study.

While it is possible for the active ingredient to be administered alone, it may be preferable to present the active ingredient as a formulation.

Formulations of the active ingredient, suitable for oral administration, may be in the form of discrete units, such as capsules, cachets, tablets, or lozenges; in the form of a powder or granules for reconstitution; in the form of a solution or a suspension in an aqueous liquid or nonaqueous liquid; or, in the form of an oil-in-water emulsion or a water-in-oil emulsion. The active ingredient also may be in the form of a bolus, electuary, or paste.

Formulations of the active ingredient, suitable for parenteral administration, may comprise a sterile, aqueous preparation of the active ingredient.

In addition to containing the standard and well known pharmaceutical carriers and/or excipients, all of the above formulations may contain other therapeutically-active substances. The formulations may be presented in unit dosage form and may be prepared by any of the methods well-known in the art of pharmacology.

The present invention is illustrated by the Examples that follow, it being understood, however, that the invention is not limited to the specific details of these Examples.

Animal Trial 1

The cerebroprotective action of citicoline was demonstrated in a model of temporary forebrain ischemia in the rat in which the middle cerebral artery (MCA) is occluded by suture. Treatment with 500 mg/kg of citicoline significantly reduced the mean volume of infarction compared with controls.

Thirty male, Sprague-Dawley rats, weighing 280–350 grams, randomly were divided into three groups of ten rats each: ten animals to be treated with 500 mg/kg citicoline; ten animals to be treated with 100 mg/kg citicoline; and ten control animals to be treated with physiological saline, the vehicle for citicoline.

All animals were anesthetized with 400 mg/kg chloral hydrate administered intraperitoneally. The left femoral artery was cannulated with PE-50 polyethylene tubing for continuous monitoring of arterial blood pressure and blood sampling for analysis of arterial blood gases. Measurements were recorded prior to surgery, one hour after ischemia, and two hours after ischemia, before reperfusion. Rectal temperature was maintained at 37° C. with a thermostatically-controlled heating lamp during the surgery and MCA occlusion.

The right MCA was occluded through a transvascular approach as previously described. See, Minematsu, K. et al. *Neurology* (1992) 42: 235–240; Zea Longa, E. et al. *Stroke* (1989) 20: 84–91. Briefly, the right common carotid artery and the right external carotid artery were exposed through a midline neck incision. The distal CCA and the external carotid artery were ligated with a 3-0 silk suture. A 4-0 monofilament nylon suture (40 mm length), whose tip had been rounded by heating near a flame and then coated with silicon (Bayer, Leverkusen, Germany), was inserted through an arteriectomy of the CCA and gently advanced into the internal carotid artery. When positioned approximately 17 mm from the carotid bifurcation, the tip of the suture occludes unilaterally the proximal anterior cerebral artery, the origins of the MCA and the posterior communicating artery. To prevent bleeding, the CCA was loosely ligated, just distal to the arteriotomy, with a 3-0 silk suture.

After 110 minutes of ischemia, the animals were treated with 500 mg/kg citicoline; with 100 mg/kg citicoline; or with 0.3 ml physiologic saline vehicle (controls), administered intraperitoneally. The MCA occluder and femoral artery catheter then were removed, after a total ischemic period of two (2) hours, permitting reperfusion of the tissue. The animals were allowed to recover from the anesthesia and to eat and drink freely. This citicoline treatment procedure was repeated for 6 additional days.

On the seventh day of treatment, the animals were reanesthetized with 400 mg/kg chloral hydrate administered intraperitoneally and then decapitated. The brains were quickly removed, inspected to confirm that no subarachnoid hemorrhage had occurred and coronally sectioned into six, 2 mm slices. The brain slices were incubated for 30 minutes in a 2% solution of 2,3,5-triphenyltetrazolium chloride (TTC) at 37° C. and fixed by immersion in a 10% buffered formalin solution. TTC stains normal brain tissue (intact cellular membrane) red; ischemic tissue, pink; and necrotic tissue, white. Six brain sections per animal were TTC-stained and photographed using a Charge Couple device camera (EDC-1000HR Computer Camera, Electrim Corporation, Princeton, N.J.), with the images stored on a microcomputer.

As brain edema is known to affect the measurement of infarct size, an image processing software package (Bio Scan OPTIMAS, Edmonds, Wash.) was utilized to calculate a corrected infarct volume. Corrected infarct area was calculated using the equation: corrected infarct area equals left hemisphere area minus (right hemisphere area minus infarct area). Corrected infarct volume was calculated by multiplying the corrected infarct area by slice thickness.

Five of ten animals in the control group died between 24 and 48 hours after MCA occlusion. Five of ten animals in the 100 mg/kg group died; four between 24 and 48 hours and one on the fifth day. Three of ten animals in the 500 mg/kg group died; two between 24 and 48 hours and one on the sixth day.

As depicted in FIG. 1, the mean volume of infarction in the control group was $243.5 \pm 88.6$ mm$^3$ (mean±SD); in the 100 mg/kg group, $200.2 \pm 19.9$ mm$^3$; in the 500 mg/kg group, $125.5 \pm 45.2$ mm$^3$. The difference of the mean values of infarct volume was significant for the control versus 500 mg/kg group ($p<0.01$, Scheffe's test). Although there was no significant difference between the control and 100 mg/kg group, there was a trend towards smaller infarction volume in the 100 mg/kg group.

Animal Test 2—Behavior

Male spontaneously hypertensive rats, SHRs, weighing approximately 250–300 g, underwent reversible middle cerebral artery (MCA) and common carotid artery (CCA) occlusion of variable duration. Briefly, with the animal under chloral hydrate anesthesia (single 0.5 g/kg i.p. bolus in 1 ml of saline provided anesthesia lasting at least 2 hours), a 0.005 inch diameter stainless steel wire (Small Parts Inc. Miami, Fla.) was placed underneath the left MCA rostral to the rhinal fissure, proximal to the major bifurcation of the MCA, and distal to the lenticulostriate arteries. The artery was then lifted, and the wire rotated clockwise. The left CCA was then occluded using two atraumatic Heifetz aneurysm clips, resulting in a reduction of blood flow in the core of the infarct (4 mm dorsal to MCA occlusion) to 4–8% of the pre-ischemic baseline value throughout the entire period of ischemia, as measured by a Vasamedics Laser Flow Blood Perfusion Monitor. After a predetermined period of CCA/MCA occlusion ranging from 0–120 minutes, reperfusion was established by first removing the aneurysm clips from the CCA, and then rotating the wire counterclockwise and removing it from beneath the MCA.

Temporalis muscle temperature was maintained at $36.5° \pm 0.3°$ C. using a heating lamp and warming blanket. Since this study was designed to analyze motor performance, we eliminated the trauma that can be produced by femoral vessel cannulation and could interfere with behavioral performance. Therefore, blood pressure, pH, PO$_2$ and pCO$_2$ changes during surgery were not recorded. Brain temperature during the entire duration of ischemia and first two hours of reperfusion was maintained at $36.2° \pm 0.4°$ C.

CDP-choline was administered 15 min after induction of ischemia with a bolus of 0.5 g/kg i.p. in 0.5–0.6 ml of 0.9% NaCl, and subsequently daily with the same dose for 14 days. Fresh CDP-choline solution was prepared every day. Control rats were injected with saline alone instead of CDP-choline solution.

Morphometric analyses were carried out 14 days after ischemia after all behavioral testing had been completed. This allowed for direct correlations between behavioral and histologic outcome in the same animals. Fourteen days after MCA/CCA occlusion, the ischemic brain is primarily characterized by the atrophy of infarcted cortical tissue. Therefore, the amount of ischemic damage can be calculated as the difference between the volume of contra- and ipsilateral cortex.

Fourteen days after ischemia, rats were sacrificed under chloral hydrate anesthesia. The brains were cooled and sectioned into 2 mm slices. The morphometric determination of the area of ipsi- and contralateral cortex of each section was performed using a computer based Drexel University (DUMAS) image analyzer calibrated to express measurement in $mm^2$. The volume ($m^2m$) of Vortices was calculated by summing the cortex area of sequential sections and multiplying by the interval thickness between sections. Finally, the volume of atrophy was calculated by subtracting the volume of ipsilateral cortex from the volume of contralateral cortex of the same rat. The investigator who performed the morphometrical analysis was blinded to the treatment regimen.

Behavioral Testing

To assess functional outcome after ischemia the following battery of tests were used, which have been validated and standardized in this model in previous studies.

Wheel: Using a rat running wheel of 12 inch diameter, and rung spacing of 2 cm, the sides of the wheel using poster board were closed, leaving a securable flap that can be opened and closed in order to place and retain the animals inside the wheel. The rats were secured inside the wheel, which itself was placed in the home cage, and then videotaped as they ran. One hundred steps taken with the forepaw contralateral to the infarcted hemisphere were observed, and the coincident number of slips of this paw between the rungs of the wheel were counted. The same observations were taken of the ipsilateral forepaw and hind limbs, and values of slips (error) per steps taken were calculated for each limb. The number of errors was then obtained by subtracting the ipsilateral errors from the contralateral ones. Each animal was tested once a day on postoperative days 4, 7, and 10.

Arm Flex: The rats were lifted by their tails so that their ventral surface was exposed to the observer for 10 seconds. The duration of asymmetrical arm flexure was timed using a stop watch. The animals were tested once a day (two trials per day) on postoperative days 1–14.

Tape Test: This test for asymmetry and recovery from asymmetry was previously described and characterized in detail by Schallert and Whishaw. Briefly, Avery self-adhesive labels (1 cm diameter circles) were placed on each forepaw of the rat, in the distal-radial region of the wrist. The time required for the animal to touch and remove each label, and the order (contralateral versus ipsilateral) in which this occurred was established and used to approximate ipsilateral asymmetry. By then affixing larger labels to the wrist less preferred and correspondingly smaller labels to the other wrist, the bias could be extinguished and simultaneously quantified, dependent upon the sizes of labels required. The bigger the ratio between surface of ipsilateral vs contralateral patches (from 1:1 to 1/8:15/8) used to neutralize bias, the higher the score (from 1 to 7) that was assigned to the rat, reflecting more extensive damage. No pretraining was performed, other than extensive handling of the animals for at least 7 days prior to the surgery. Each animal was tested on postoperative days 2–3 (one trial per day).

Prior to surgery and thereafter, all animals were kept in their individual cages in an isolated room that provided a minimally stressful environment. At least two weeks of adaptation, during which animals were handled by the same investigator, who carried out all behavioral testing, was done on a daily basis (at least 10 min a day for each animal). This adaptation was introduced to reduce the stress response to touch and handling, and was crucial, especially for appropriate execution of the tape test. The investigator who performed the behavioral testing was blinded to the treatment regimen.

Composite Behavioral Abnormality Score

A behavioral abnormality score was calculated, which represented a composite of the three individual tests and used the number of errors (slips/steps; wheel), time (arm flex), or score (surface area necessary to extinguish bias; tape test), to quantitate behavioral dysfunction.

First, an average value of the performance of each rat in each test over time was calculated. Within each behavioral test, the two lowest values were averaged and subtracted from the average of the two highest values. This range was then divided into five equal quantities, and subsequently scored from 0 to 4. Next, we determined the composite score of all 3 tests, assigning equal weight to each of them. Each rat was therefore scored on three separate tests and given a composite score of performance, for a maximum score (deficit) of 3×4=12.

Correlation Between Duration Of Ischemia And Infarct Volume Or Behavioral Abnormality The behavioral abnormality score and calculated atrophy volume ($mm^3$) were used to obtain a correlation between duration of ischemia and behavioral abnormality score or atrophy volume in untreated and CDP-choline treated animals.

Composite score values or atrophy volumes were entered into the computer and analyzed by the curve fitting computer program ALLFIT to generate a curve describing the correlation between behavioral abnormality/atrophy volume and duration of ischemia in terms of maximal behavioral dysfunction/maximal atrophy volume ($BD_{max}\backslash Vol_{max}$) produced by prolonged ischemia, the time necessary to induce half maximal behavioral dysfunction/atrophy volume ($BD_{50}\backslash T_{50}$), as well as curve shape and steepness. The computer program (ALLFIT) employed to perform this analysis used the logistic function $y=(a-d)/[1+(xXc)b]+d$, where y is the behavioral abnormality score, x is the duration of ischemia, a is the response when x=0, d is the $BD_{max}$–$Vol_{max}$, b is a "slope factors that determines the steepness of the curve, and c is the $BD_{50}/T_{50}$. This program was developed for the simultaneous fitting of families of sigmoidal dose response curves, and was obtained from the Laboratory of Theoretical and Physical Biology at NIH.

Statistical Analysis

The statistical difference in $BD_{50}/T_{50}$ and $BD_{max}$ –$Vol_{max}$ between the groups was calculated, employing log of the mean and log of the standard error of compared values provided by ALLFIT, and was assessed using Student's t-test.

RESULTS

Histology—Analysis Of The Volume Of Atrophy

Eighteen and 23 rats were analyzed in saline control and CDP-choline treated groups, respectively. CDP-choline administered for 14 days significantly ($p<0.05$) extended the duration of ischemia before reperfusion that produced half maximal atrophy ($T_{50}$).

The $T_{50}$, computed by the ALLFIT program, for control (untreated) animals was 38.3±5.9 min. and for CDP-choline treated animals was 60.5±4.3 min. CDP-choline did not, in this model, reduce maximal infarct volume; $Vol_{max}$ was 103.3±13.6 $mm^3$ vs 101.6±11.4 $mm^3$ for control and CDP treated groups, respectively.

The above results suggest that CDP-choline can reduce morphological injury primarily after relatively short durations of ischemia, which produce submaximal injuries. These results also emphasize the criticality of administering citicoline shortly after the occurrence of the ischemic event, i.e., as soon as possible.

Behavioral Analysis

Sixteen untreated and 21 CDP-choline treated rats were analyzed. CDP-choline treatment significantly prolonged $BD_{50}$, in a similar fashion to that observed in the histological analysis. $BD_{50}$ in control rats was 41.9±4.6 min. while CDP-choline treatment extended $BD_{50}$ by approximately 30 min. to 72.9±24.5 min.

There was no significant effect of CDP-choline treatment on $BD_{max}$; values were 8.5±0.7 and 10.1±4.0 for control and CDP-columna treated animals, respectively.

These data indicate that chronic CDP-choline treatment provides significant improvement of both histological and functional outcome by extending $T_{50}$ and $BD_{50}$. CDP-choline, however, did not in this case influence $Vol_{max}$ and $Bd_{max}$. These results suggest that the effectiveness of CDP-choline is greater in animals demonstrating submaximal ischemic injury, which in this model is produced by 30–75 min of ischemia.

Double-Blind, Placebo-Controlled Clinical Trials

Based upon review of two clinical trials and 17 trials reported in the literature, citicoline (doses ranging from 250 to 400 mg/day) consistently appeared to be well tolerated among stroke and head trauma patients dosed from five days to eight weeks. Based upon a review of over 50 trials reported in the literature, citicoline consistently appeared to be well tolerated among other populations as well. Adverse events were generally clinically unimportant except in the cases where death ensued due to the severity of the ischemia (which is not unexpected in the populations studied). No clinically important changes have been reported in laboratory parameters, vital signs, or electrocardiograms.

This trial was designed to evaluate the effect of three doses of citicoline (500 mg, 1000 mg and 2000 mg) versus placebo in patients who had experienced an acute ischemic stroke.

Dosing Instructions/Schedule

If randomized before 3:00 pm, patients were given two tablets upon entry into the study and two tablets at the next mealtime for a total of four tablets on entry day. Otherwise, the patient was given two tablets (morning dose) upon entry, and the other two tablets for Day 1 (evening dose) were unused and returned. For the remainder of the study, patients were given two tablets in the morning and two tablets in the evening (See Treatment Regimen, which follows). For patients unable to ingest the study tablet whole, acceptable routes of administration include nasogastric administration or crushing tablets and mixing with food or beverage.

Treatment Phase

Study drug was administered twice daily (two tablets in the morning and two tablets in the evening) for six weeks.

The effectiveness of the various dose levels of citicoline was assessed by the Barthel Index.

The secondary efficacy assessments collected during this study include the Barthel Index at Week 12 (with a score of at least 61 considered a success), Modified Rankin Score, NIH Stroke Scale total, NIH Stroke Scale motor item, the number of days to discharge from the hospital, mortality, and other neuropsychological battery scores. The NIH Stroke Scale and Barthel Index are standard measurements of stroke symptoms and functional abilities related to daily living.

The double blind, placebo-controlled trial showed that patients who received 500 milligrams of citicoline daily were more than twice as likely to manifest minimal or no disability at 12 weeks following stroke as patients who received placebo, as measured by the NIH Stroke Scale, and 1.6 times as likely to manifest minimal or no disability as measured by the Barthel Index.

Diffusion Weighted MRI (DWI) Studies

DWI detects, within minutes after onset of ischemia, regions of ischemic injury and animal models have demonstrated the utility of DWI is monitoring neuroprotective therapy. Placebo-controlled trials suggest that citicoline reduces infarct size in a rat temporary occlusion model as described above.

In this study, twelve patients were studied from a Phase III double blind placebo controlled trial of citicoline (500/1000/2000 mg daily po for 6 weeks) in acute stroke (MCA territory, less than 24 hours from onset). The design and results of the overall study are presented above. Multislice echo planer DWI and T2-weighted MRI was performed at acute and chronic time points. That is, DWI scans at baseline (i.e., between 8 and 24 hours after symptom onset, the presumed time of stroke) and at least one more image on treatment were taken. The mean time to follow up was 9.3 weeks (range 4.1–26.3 weeks; median 6.6 weeks). Lesion volumes were measured on two occasions by three observers blinded to treatment and clinical information about the patients. The percent change in the infarct volume between the baseline scan and the second scan after treatment was then determined.

Three of four placebo patients showed growth of the lesion, whereas seven of the eight patients treated with citicoline showed a reduction in lesion volume (4/5 at 500 mg; 3/3 at 2000 mg). A Chi-squared test for trend based on dose was significant at p=0.031. These determinations were compared to a series of historical control patients (n=31) collected in the same manner. Of the 31 patients, 22 increased infarct volume, 7 decreased infarct volume and 2 had no change. Of the 4 placebo patients in the present study, 3 increased infarct volume and 1 decreased infarct volume, exactly the proportion of the historic control. Of the 8 patients treated under the practice of the invention (5 on 500 mg qd, 3 on 1000 mg bid), 7 decreased infarct volume and 1 increased infarct volume.

The proportion of patients who decreased infarct volume under the practice of the invention was tested against the proportion in the historic control (i.e., 22/7 vs. 1/7) using Fishers Exact Test, with the difference favoring the invention being found significant (p=0.0021). As evaluated by DWI, these trials thus indicate a significant reduction of infarct volume upon treatment of the ischemia with citicoline when the treatment is initiated as early as possible after the ischemic episode and continuing for a period of up to several weeks.

What is claimed is:

1. A method of protecting brain tissue from cerebral infarction subsequent to ischemia comprising administering to a subject in need thereof a first dose of an effective amount of citicoline or a pharmaceutically acceptable salt thereof, excluding effective amounts of cytidine diphosphoethanolamine, cytidine diphospho-N-methylethanolamine, cytidine diphospho-N,N-dimethylethanolamine, or mixtures thereof, no later than about 24 hours after the occurrence of said ischemia, followed by the administration of subsequent doses of effective amounts of citicoline or a pharmaceutically acceptable salt thereof over a period of at least about a week.

2. The method of claim 1 in which said first dose is administered within about 12 to about 15 hours after the occurrence of said ischemia.

3. The method of claim 1 in which said first dose is followed by subsequent doses of citicoline or a pharmaceutically acceptable salt thereof over a period of at least about 14 days.

4. The method of claim 1 in which said first dose is followed by subsequent doses of citicoline or a pharmaceutically acceptable salt thereof over a period of at least about 30 days.

5. The method of claim 1 in which said first dose is followed by subsequent doses of citicoline or a pharmaceutically acceptable salt thereof over a period of at least about 4–8 weeks.

6. The method of claim 1 in which said first dose is followed by subsequent doses of citicoline or a pharmaceutically acceptable salt thereof over a period of at least about 6 weeks.

7. The method of claim 1 in which said effective amount ranges from about 100 mg to about 2000 mg of citicoline or its pharmaceutically acceptable salt.

8. The method of claim 7 in which said effective amount ranges from about 500 mg to about 1000 mg of citicoline or its pharmaceutically acceptable salt.

9. The method of claim 1 in which said first dose or subsequent doses is administered one or more times daily over said period.

10. The method of claim 9 in which said first dose or subsequent doses is administered twice daily over said period.

11. The method of claim 1 in which said ischemia occurs in the brain.

12. The method of claim 1 in which the subject is human.

13. The method of claim 1 in which the subject has suffered a stroke.

14. The method of claim 1 in which the subject has suffered a head trauma.

15. A method of protecting brain tissue from cerebral infarction subsequent to ischemia comprising administering to a subject in need thereof a first dose of an effective amount of citicoline or a pharmaceutically acceptable salt thereof, excluding effective amounts of cytidine diphosphoethanolamine, cytidine diphospho-N-methylethanolamine, cytidine diphospho-N,N-dimethylethanolamine, or mixtures thereof no later than about 24 hours after the occurrence of said ischemia, followed by the administration of subsequent doses of effective amounts of citicoline or a pharmaceutically acceptable salt thereof over a period of at least about 5–8 weeks.

16. The method of claim 15 in which said effective amount ranges from about 500 mg to about 1000 mg.

17. The method of claim 15 in which said first or subsequent doses is administered once or twice daily over said period.

* * * * *